United States Patent [19]

Lacy

[11] Patent Number: 5,573,747
[45] Date of Patent: Nov. 12, 1996

[54] METHOD FOR PREPARING A PHYSIOLOGICAL ISOTONIC PET RADIOPHARMACEUTICAL OF $^{62}$CU

[76] Inventor: Jeffrey L. Lacy, 15019 Penn Hills, Houston, Tex. 77062

[21] Appl. No.: 444,957

[22] Filed: May 19, 1995

[51] Int. Cl.$^6$ .......................... A61K 51/00; A01N 47/34
[52] U.S. Cl. .......................... 424/1.65; 424/1.11; 514/582
[58] Field of Search ...................... 424/1.65, 1.11, 424/9.1; 514/582

[56] References Cited

U.S. PATENT DOCUMENTS

| | | | |
|---|---|---|---|
| 3,265,570 | 8/1966 | Michaels | 514/582 |
| 3,505,456 | 4/1970 | Barrett | 514/582 |
| 5,057,302 | 10/1991 | Johnson et al. | 424/1.65 |
| 5,240,693 | 8/1993 | Born et al. | 424/1.65 |
| 5,342,604 | 8/1994 | Wilson et al. | 424/1.65 |
| 5,393,512 | 2/1995 | Vanderheyden et al. | 424/1.11 |

OTHER PUBLICATIONS

Cappucino et al (1968). Cancer Research, vol. 28, No. 10, pp. 1923–1931. "Fate of Pyruvaldehyde Bis(thiosemicarbazone)–$^{35}$S in Male and Female Rodents".

Herrador et al (1987). Analyst, vol. 112, pp. 1237–1246. "Spectro–photometric Determination of zinc in potable waters and Insulin with Methylglyoxal Bis (4–phenyl–3–thiosemi–carbazone)".

Giessen et al (1973). J. National Cancer Institute, vol. 51, pp. 139–146. "Effect of Heavy Metal on the In Vitro Cytotoxicity of 3–ethoxy–2–oxobutyr–aldehyde bis (thiosemicarbazone)".

Primary Examiner—John Kight
Assistant Examiner—Dameron L. Jones
Attorney, Agent, or Firm—Pravel, Hewitt, Kimball & Krieger

[57] ABSTRACT

A method of preparing a radiopharmaceutical in a form suitable for intravenous bolus injection is disclosed. The method comprises eluting $^{62}$Cu from from an anion exchange column loaded with $^{62}$Zn.

8 Claims, 2 Drawing Sheets

METHOD FOR PREPARING A PHYSIOLOGICAL ISOTONIC PET RADIOPHARMACEUTICAL OF $^{62}$CU

Positron emission tomography (PET) imaging is a powerful medical imaging technique with well established advantages over current widely practiced nuclear imaging techniques.

The positron emission tomography (PET) imaging technique possesses substantial advantages over the widely used single photon imaging. These include full intrinsic three dimensional character, freedom from the substantial attenuation effects of the single photon technique, and a potentially wider variety of radiopharmaceuticals with uptake characteristics mimicking biological functions. Despite these intrinsic advantages the PET technique has not yet developed into a practical clinical tool because of its reliance upon in-hospital cyclotron production of radiopharmaceuticals. Such production adds a substantial cost burden and also is mired, and most likely will continue to be mired, in regulatory problems. Less than one hundred North American PET facilities are currently in operation, and the average facility is performing only a few clinical studies each day.

This lack of growth is directly attributable to the current dependence of such facilities upon in-hospital cyclotrons for production of radiopharmaceuticals. Such in-hospital cyclotrons increase cost substantially, both because of high initial expense of the facility, as well as high on-going operational expenses. Thus, procedure cost is assured to be many times that of standard nuclear medicine imaging requiring no such facility. Even the well documented advantages of PET likely will not justify such high expense, particularly in the current climate of health care cost containment.

Perhaps, just as importantly, such in-hospital radiopharmaceutical production carries with it another potentially insurmountable problem. All Food and Drug Administration (FDA) approved radiopharmaceuticals currently are produced in central commercial facilities under very well controlled conditions and distributed to local clinics where they are administered. Production of radiopharmaceuticals by numerous widely distributed in-hospital cyclotron facilities is a concept which is not and may never be embraced by the FDA in any practical framework.

Radionuclide generator systems on the other hand which can be produced in one well controlled facility and distributed, are readily embraced by current FDA procedures, and have a long history of successful clinical application. A generator uses a parent-daughter (P/D) nuclidic pair wherein a relatively long-lived parent (P) isotope decays to a short-lived daughter (D) isotope that is used for imaging. The differing chemistry of the parent isotope—which is produced at a cyclotron facility—is utilized for its adsorption to a column material which may be shipped to a clinical site and from which the daughter isotope may be eluted at the site of clinical use. Such P/D generator systems for production of short lived radionuclides combined with regional production and distribution of longer lived agents, such as $^{18}$F-FDG, may represent a viable solution to the development of the powerful PET technique as a clinically practical tool.

The $^{82}$Sr/$^{82}$Rb generator is an FDA approved, commercially available system. Despite its availability for several years, it has had little or no impact upon wider utilization of PET. The primary problem with it is the high production cost of the $^{82}$Sr parent isotope which is dependent upon very high energy production sites, such as Los Alamos. Also, the very short 76 second half-life of the $^{82}$Rb isotope imposes some significant limitations. In cardiac imaging, which is the major role of $^{82}$Rb, once time is allowed for blood clearance only a very brief period is left for image acquisition. This necessitates very high rate imaging in order to achieve adequate statistics, which is incompatible with many low cost PET cameras. The short 76 second half-life of $^{82}$Rb also essentially prevents practical synthesis processes which could be utilized to broaden the application areas beyond cardiac perfusion imaging. The scope of such synthesis processes is also substantially restricted by the limited chemistry of Rb.

The $^{68}$Ge/$^{68}$Ga generator has been commercially available, although not FDA approved, for many years. It also has had little impact in the PET field. The lengthy 68 minute half-life of $^{68}$Ga is compatible with synthesis procedures. However, clinically useful $^{68}$Ga radiopharmaceuticals have not been forthcoming although there has been some recent progress in this area. In addition, the 68 minute half-life of $^{68}$Ga is not optimally compatible with back-to-back imaging procedures which are important in such applications as cardiac perfusion imaging. In such practice, baseline and intervention imaging are compared and must be accomplished in a reasonable clinic visit time without interference. The 68 minute half-life of $^{68}$Ga can also cause interference with other agents such as $^{18}$F-FDG, which may be utilized in conjunction with a perfusion agent to assess tissue viability preventing such combined studies from being done even within the same day.

A $^{178}$W/$^{178}$Ta generator for the production of physiologically acceptable solutions of $^{178}$Ta (9.3 min. half-life) has also been described in U.S. Pat. No. 4,830,848. Further, a design for the automated elution and buffering of $^{178}$Ta by peristaltic pump feeding of the required solutions into a physiologically acceptable solution that is directly delivered into an injection syringe has been proposed. *Journal of Nuclear Medicine*, Vol. 32, No. 11, pp. 2158–2161 (1991). The $^{178}$Ta may after elution and buffering be used directly for imaging without the need for further synthetic manipulation. Its use for imaging, however, is limited to a new multiwire gamma camera because of its relatively low energy (60 keV).

The 9.7 minute half-life of $^{62}$Cu as a daughter isotope produced from a $^{62}$Zn parent isotope of 9.26 hour half-life is nearly ideal for many PET procedures. Chemical modification of the $^{62}$Cu eluted from a $^{62}$Zn/$^{62}$Cu generator is required for any meaningful clinical imaging. The half-life of $^{62}$Cu is long enough to facilitate radiopharmaceutical synthesis procedures, even ones of some complexity. At the same time, it is short enough that multiple back-to-back imaging procedures are practical during a reasonably brief interval without interference of $^{62}$Cu background activity from a previous injection. Also such studies can be followed by another agent such as $^{18}$F-FDG after a reasonable delay, on the order of 40 minutes.

The diverse coordination chemistry of copper makes possible a wide variety of $^{62}$Cu radiopharmaceuticals (Robinson 1980). A promising example of such agents, $^{62}$Cu-PTSM, has been developed (Petering 1964, Green 1987, 1990). This agent has been shown to have utility as a myocardial, cerebral, renal and tumor perfusion agent (Green 1990, Mathias 1990, 1991).

Unlike some of the other radio isotopes which are useful by virtue of their natural biodistribution; $^{62}$Cu must be bound to a carrier molecule or ligand in order to carry it to specific sites for meaningful imaging. Hence, in addition to eluting the daughter $^{62}$Cu isotope from a column material to which its parent isotope $^{62}$Zn is adsorbed, the $^{62}$Cu so eluted must also thereafter be synthetically manipulated to form a $^{62}$Cu-ligand complex that is in the form of a physiological isotonic solution. Green et al., *Journal of Nuclear Medicine*, Vol. 31, No. 1, pp. 1989–1996 (1990) describes a $^{62}$Zn/$^{62}$Cu generator from which $^{62}$Cu is eluted by concentrated chloride solution, then buffered with sodium acetate and mixed with alcoholic stock solution of pyruvaldehyde bis($N^4$-methylthiosemicarbazone)—i.e. H$_2$ (PTSM)—and allowed to react, thereafter the reaction solution is passed through a solid-phase extraction cartridge to isolate the $^{62}$Cu-ligand product ($^{62}$Cu-PTSM) from the hypertonic reaction mixture, and the $^{62}$Cu-ligand product is recovered by an ethanol backwash and then diluted with saline to a 5% ethanol concentration to prepare it for patient use. All elution and synthetic manipulations are manually accomplished, exposing the sample preparer to radiation and prolonging the time between elution of the $^{62}$Cu and the time at which a physiological isotonic solution of the $^{62}$Cu-PTSM complex is ready for utilization for patient imaging. Carla et al., *Appl. Radiat. Isot.*, Vol. 42, No. 3, pp. 317–320 (1991) describes a remote system for the synthesis of copper-62 labeled Cu(PTSM) which may be shielded to reduce worker radiation exposure to acceptable levels. The synthetical procedure employed is like that "hands on" procedure described by Green et al., but the remote system operates at a somewhat slower pace with a synthesis time of 7–8 minutes providing a product of 40% end-of-synthesis radiochemical yield based upon $^{62}$Cu activity available at end of elution.

SUMMARY OF THE INVENTION

The present invention comprises methods for preparing a $^{62}$Zn isotope, adsorbing the $^{62}$Zn isotope upon an anion exchange resin as a column material to yield a $^{62}$Zn/$^{62}$Cu generator eluting $^{62}$Cu from the generator in an amount of an eluant to provide an eluate having a radioactivity of about 0.1 to 10.0 mCi/ml, and rapidly synthetically modifying the $^{62}$Cu of the eluate into a $^{62}$Cu-ligand complex solution and then altering the $^{62}$Cu-ligand complex solution into a physiologically acceptable isotonic solution ready for I.V. bolus injection for PET imaging of a patient. In a preferred embodiment of the invention $^{62}$Cu is eluted from a $^{62}$Zn/$^{62}$Cu generator comprising an anion exchange resin loaded with $^{62}$Zn by a small volume of a concentrated chloride solution of a pH of less than 2, the $^{62}$Cu eluate is immediately mixed with an acceptable buffer solution (such as sodium acetate or sodium citrate) to achieve a pH of from about 5 to about 7 and the so-buffered solution then immediately mixed with a quantity of a ligand compound solution and thereafter mixed with water in a quantity sufficient to reduce the chloride content of the fluid to a physiological isotonic level, i.e., about 0.15N anion content, thus forming a physiologically isotonic solution ready for immediate I.V. bolus injection. Further, in a preferred embodiment of the invention, an automated module incorporating a four-channel peristaltic pump that provides for delivery of a pyrogen free eluant, buffer solution, ligand compound solution and water, is utilized for pump control and flow of the different solutions, for the automated rapid preparation of a physiological isotonic solution of a $^{62}$Cu-ligand complex that is ready for I.V. bolus injection.

In accordance with the invention, a sterile pyrogen free physiological isotonic solution of a $^{62}$Cu-ligand complex ready for I.V. bolus injection may be rapidly prepared—ready within less than about 45 seconds after elution of $^{62}$Cu from the $^{62}$Zn/$^{62}$Cu generator—automatically, with appropriate shielding to protect clinic personnel from undue radiation exposure, and with a minimum of decay in the activity level of the $^{62}$Cu eluted from the generator before it is ready as a $^{62}$Cu-ligand complex for patient use for PET imaging. Further, the preferred method of sample preparation minimizes the possibility that undesirable contaminants will become entrained in the patient ready isotonic solution by reason of the steps necessary to synthetically modify the $^{62}$Cu required for PET imaging.

DESCRIPTION OF THE PREFERRED EMBODIMENTS

Figure 1:
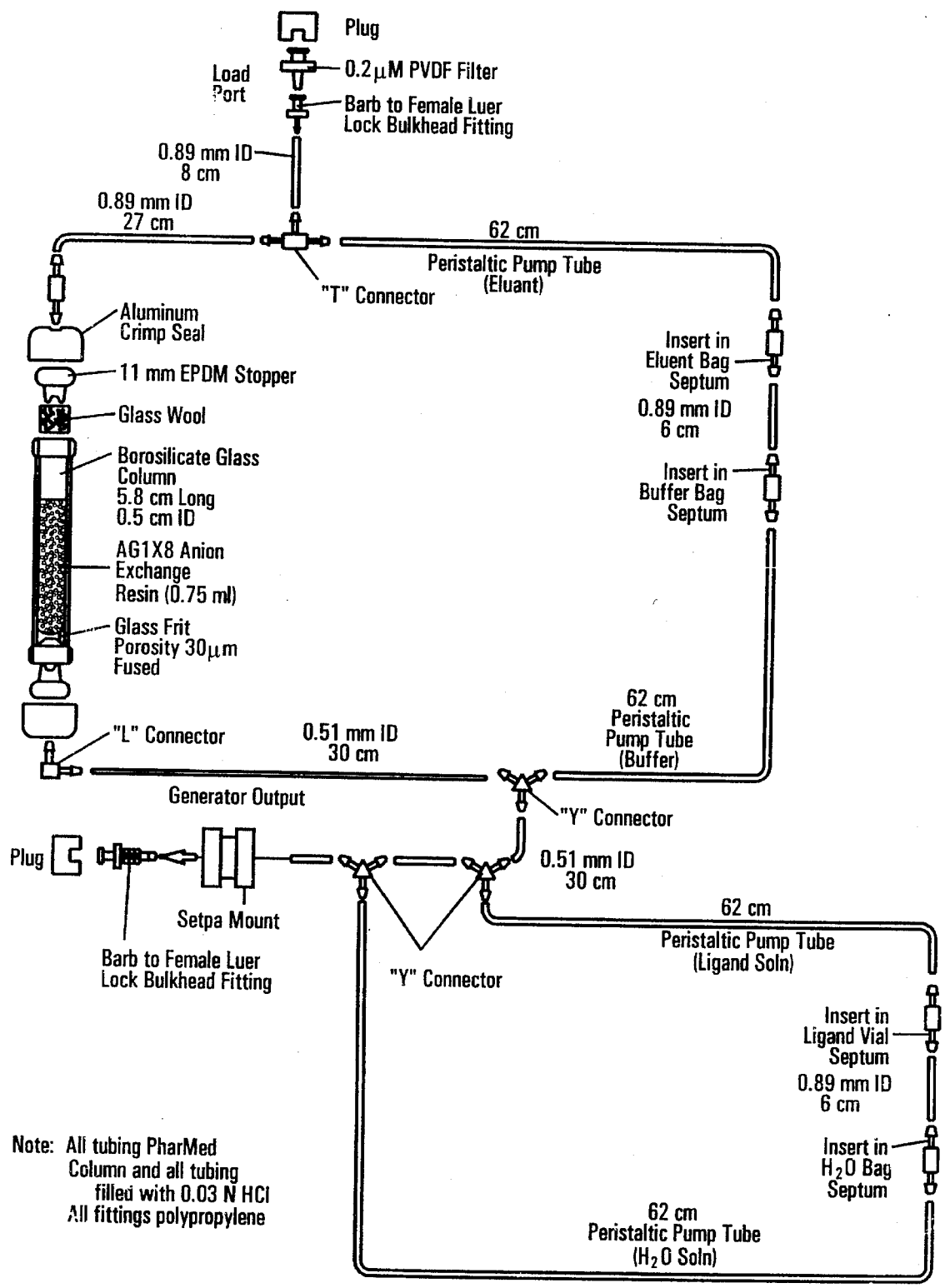
FIG. 1 illustrates a $^{62}$Zn/$^{62}$Cu generator column and accessory plumbing assembly suitable for autoclaving.

The key obstacle to a practical $^{62}$Zn/$^{62}$Cu generator is the short 9.3 hour half-life of the parent isotope $^{62}$Zn. In the production of this generator the cyclotron target must be irradiated and processed very quickly to produce purified $^{62}$Zn which must then be quickly loaded onto the anion exchange resin of the generator column. This generator system must then be assessed for proper function and shipped to the clinical site user overnight. It can only be utilized for one day and thus must be put into service at the clinical site the day of receipt. This requires it to be modular and automated for exceptional ease of use.

The key to viability of a $^{62}$Zn/$^{62}$Cu generator as a practical clinical tool is development of an economical system which can be delivered anywhere in the continental United States. A desired scenario is as follows: 1) irradiate target at cyclotron facility late in the morning with end of bombardment (EOB) at 12:00 noon, 2) cool target for two hours, 3) receive target at the production facility by 3:00 pm, 4) process, load generator column, quality-assurance check and pack the $^{62}$Zn/$^{62}$Cu generator in shipping container by 7:00 pm, 5) deliver to shipper by 8:00 pm and 6) shipper delivers to the clinical site by 8:00 am the next day. Such delivery can be provided in most U.S. metropolitan areas on Tuesday through Friday, and optionally on Saturday.

Production of $^{62}$Zn is achieved through proton irradiation of natural Cu targets utilizing both the $^{63}$Cu(p,2n) and the $^{65}$Cu(p,4n) reactions. Following a cool down period of 3–4 hours, the Cu target is processed to recover $^{62}$Zn. The principle co-produced isotopes are $^{63}$Zn ($t_{1/2}$=38 min) produced via $^{65}$Cu (p, 3n) and $^{61}$Cu ($t_{1/2}$=3.4 h) produced via $^{63}$Cu (p, 3n) $^{61}$Zn ($t_{1/2}$=89 s)→$^{61}$Cu. The 3–4 hour cool down period is ample to reduce $^{63}$Zn to a near negligible level. However, $^{61}$Cu is not significantly reduced in the 3–4 hours and is the most significant background radiation source. Allowing ample cool down time for this longer lived contaminant is not practical since it would impact significantly the production cost of the 9.26 hr half-life $^{62}$Zn isotope. In addition to $^{62}$Zn, several Cu, Ni, and Co radionuclides are produced. They must be removed in the purification process along with the natural copper.

Production of $^{62}$Zn and $^{65}$Zn. A Cu foil stack consisting of 10 foils of thickness 0.015" was irradiated at 40 MeV to an integrated current of 0.033 μA-hr. Gamma ray spectra were collected from each of these foils over a 7 day interval and the levels of the isotopes $^6$Cu, $^{64}$Cu, $^{62}$Zn, $^{63}$Zn, $^{65}$Zn, $^{58}$Co and $^{57}$Ni were quantified. Production of the unwanted $^{61}$Cu falls rapidly as the incident energy is degraded while $^{62}$Zn production is reduced only slightly. The near optimal compromise between reduction of $^{61}$Cu and loss of $^{61}$Zn is achieved at 30 MeV instant beam energy. Production rates of $^{62}$Zn and $^{65}$Zn were determined for the 24.5 MeV to 40 MeV energy range (0.064" target thickness) by irradiation of the Cu target for 10 μA-hr. The 1.85 g Cu target was dissolved in C HNO$^3$ and converted to 2M HCl. Separation of $^{62}$Zn and $^{65}$Zn was achieved using a 2 ml gravity fed AG1x-8 anion exchange resin column (Bio-Rad, Richmond, Calif.). The complete dissolved target solution (10 ml) was passed through the column and followed by 10 ml 2M HCl. The Zn isotopes were recovered from the column through elution with 8 ml of H$_2$O. By measuring the entire separation column activity the yield of $^{62}$Zn wash from the column was greater than 99.95%. The loss of $^{62}$Zn in the dissolved copper solution was assessed by passing the solution through a second freshly prepared AG1x–8 anion exchange column. Following wash of the column with 10 ml of 2M HCl solution the entire column was measured in the Capintec dose calibrator. The $^{62}$Zn retained on this column was less than 0.5% of that recovered in the initial separation. Therefore the overall recovery of $^{62}$Zn was greater than 99%. The total recovered $^{62}$Zn adjusted to end of bombardment (EOB) was 68.05 mCi giving a $^{62}$Zn production rate of 6.8 mCi/μA-hr. The total recovery of $^{65}$Zn was 25 μCi, giving a $^{65}$Zn production rate of 2.5 μCi/μA-hr. Production rates were also measured for the optimized condition of 33 MeV irradiation of 0.064" Cu by HPGe measurements on product from the final process apparatus. These values were 10.74 mCi/μA-hr $^{62}$Zn and 45.68 μCi/μA-hr $^{65}$Zn.

Co-produced Radioisotope Yields. Since radiation shielding and radioactive waste issues are typically dominated by coproduced radioisotopes, a detailed analysis of such production has been carried out. The relative activity measurements (Capintec 760) of the entire Cu waste vial from the run described above was plotted out to 900 hours. This decay data is well fitted by a multi-exponential curve including the four radioisotopes, $^{61}$Cu (3.37 h), $^{64}$Cu (12.71 h), $^{57}$Ni (36.1 h), and $^{58}$Co (70.8 d). The production rates of each of these isotopes at EOB were determined through HPGe spectroscopy and are tabulated in Table 1 below for both 40 MeV and 33 MeV on 0.064" Cu.

TABLE 1

| Isotope | Production Rate (mCi/μA-hr) Protons on 0.064" Cu Target | | |
|---|---|---|---|
| | 33 MeV | 40 MeV | ≧511 keV γ |
| $^{61}$Cu (3.4 h) | 31.2 | 117.8 | 141% |
| $^{64}$Cu (12.7 h) | 23.6 | 29.4 | 36% |
| $^{63}$Zn (38.1 m) | 328.5 | 180.4 | 201% |
| $^{62}$Zn (9.26 h)/$^{62}$Cu | 8.63 | 6.80 | 268% |
| $^{58}$Co (71 d) | .0099 | .0977 | 130% |
| $^{65}$Zn (244 d) | .0334 | .0025 | 53% |
| $^{57}$Ni (36 h) | 0.0141 10$^{-3}$ | 0.293 × 10$^{-3}$ | 180% |

Radiation shielding issues are strongly dominated by the $^{61}$Cu radionuclide since same day processing and $^{62}$Zn production cost issues mandate its presence during the processing at a level far exceeding the $^{62}$Zn levels. This isotope decays predominantly by β$^+$ and thus the principle shielding issue is 511 keV gamma rays. Although $^{64}$Cu is also copiously produced, it plays a lessened role in radiation safety issues since its positron emission abundance is only 18% and essentially no other gamma emissions are present.

The $^{65}$Zn and $^{58}$Co isotopes dominate the long term radioactive waste disposal issue. The production levels of these isotopes are easily compatible with storage to complete decay. The $^{65}$Zn by-product will be removed from generator modules by water wash, concentrated and stored to complete decay. Since $^{58}$Co can be easily separated from Cu by anion exchange chromatography, this waste can also be separated in carrier free form and stored in a very small volume container with tolerable shielding requirements. Both of the co-produced isotopes, $^{64}$Cu and $^{58}$Co, represent potential commercial opportunities as by-products of this process.

$^{62}$Zn Purification Process Development. Through repeated cold target dissolution it was found that 10 ml of C HNO$_3$ combined with carefully staged beaker heating provided complete and consistent target dissolution in less than 15 min. The resulting process is very controlled and essentially no splatter occurs. Most of the empiric work focused upon the conversion of the HNO$_3$ solution to 2M HCl in preparation for the column separation process. Beaker heating cycle, schedule of addition of C HCl and endpoints of evaporation cycles were varied through a total of 7 cold target processes. The resulting process produced with complete consistency a 10 ml 2M HCl solution ready for column chromatography in a time of 2.5 hours from the beginning of the dissolution process. All hot target runs were performed using this procedure which involved no qualitative adjustments based on beaker observation. All additions of reagents and hot plate temperature adjustments were performed on a rigorous time schedule making the entire procedure compatible with complete computer control with remote operator observation only.

Separation of $^{62}$Zn from the natural copper target material and other radionuclide impurities was accomplished by passing the dissolved target solution in 2NHCl through a small anion exchange column filled with AG 1×8 (200–400 mesh) resin. The column elution began by pumping 5 column volumes of dissolved copper target solution through the column. A 2 ml addition of 2M HCl to BK1, used to collect any remaining target solution from the beaker, was also pumped through the column. Then 5 column volumes of 2M HCl was passed through the column to flush all the copper solution, leaving only the Zinc, which strongly binds to the resin in the column. Finally, the zinc was washed off the column with 4 column volumes of H$_2$O. A highly consistent and acceptable loss of $^{62}$Zn of tracer ranging from 3–3.5% was obtained. Following elution with H$_2$O the column was flushed with 2M HCl and left in a sealed condition ready for the next process. Following elution of $^{62}$Zn from the separation column directly into beaker 10, the H$_2$O solution is evaporated to dryness, the beaker is allowed to cool briefly and the $^{62}$Zn is brought up into 2 ml 2M HCl. This final product solution is then transferred to a shielded product tube and is ready for loading onto the $^{62}$Zn/$^{62}$Cu generator.

In summary the entire process from target dissolution through column separation has been developed and may be implemented in a dedicated process cell developed exclusively for the purpose. All aspects of the process are completely compatible with computer controlled automated operation with remote operator observation only. The total time required from dissolution of the target through preparation of the purified $^{62}$Zn solution ready for loading on a generator column is 4 hours. This is compatible with economic same day process and generator delivery with acceptable impact upon accelerator production cost.

$^{62}$Zn/$^{62}$Cu Generator. Chloride form AG1×8 (200–400 mesh) anion exchange resin purchased from Bio Rad Laboratories (Richmond, Calif.) was typically used as the resin for the generator. Concentrated nitric acid (AR Select), concentrated hydrochloric acid (AR Grade), sodium chloride (USP, TAC), and sodium acetate trihydrate (USP, TAC) were obtained from Mallinckrodt, St. Louis, Mo. Water (Reagent grade) used in the preparation of reagents for the radiochemical processing was obtained from Ricca Chemical Co, Arlington, Tex. Sterile water for preparation of the generator solutions was obtained from McGaw, Inc., Irvine, Calif. Ethyl alcohol (USP) was obtained from AAPER Alcohol and Chemical Company, Shelbyville, Ky. High purity copper foil (A102, 99.95%) was obtained from Farmers Copper, Galveston, Tex. Generator yield measurements were performed with a Capintec model CRC7 dose calibrator. As the ligand compound for synthesis of a $^{62}$Cu-ligand complex, pyruvaldehyde bis($N^4$-methylthiosemicarbazone) was chosen for use and was dissolved in a water-ethanol solution comprising 15% ethanol to a concentration of 1.5 µg/ml. Generator breakthrough measurements were made by NaI well counting (Searle Model 1197). Radiochemical purity measurements were performed by high resolution gamma ray spectroscopy with a high purity germanium (HPGe) reverse electrode detector (Canberra, Inc., Model GR0820, 8%) and a personal computer analyzer (Canberra, Inc., Signal Processor Model 1510, System 100 Master Board Model 4610). Assessment of the chemical identity, purity and synthesis yield of the 62Cu-PTSM complex was performed by thin layer chromatography (ethanol).

Figure 2:
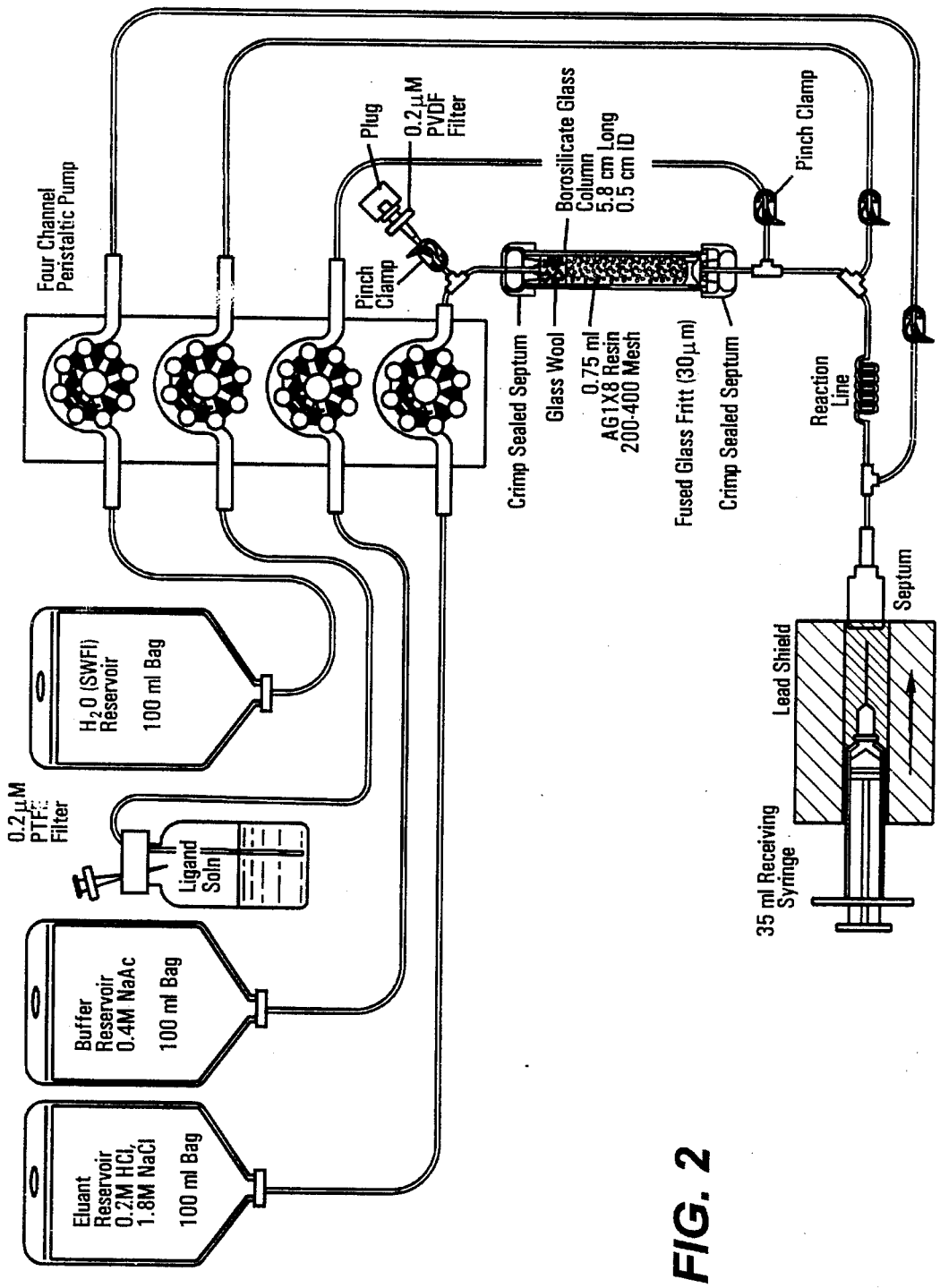
FIG. 2 illustrates a module for the automated elution of $^{62}$Cu from the $^{62}$Zn/$^{62}$Cu generator and treatment of the eluate to synthesize the $^{62}$Cu content thereof into a $^{62}$Cu-ligand complex in a sterile pyrogen free physiologically isotonic solution ready for I.V. bolus injection.

The generator column and plumbing set developed for the $^{62}$Zn/$^{62}$Cu generator is shown in FIG. 2. This tubing set was filled with 0.03N HCl completely sealed and autoclaved with integral 0.2 µm filter in place. The set includes two pump lines one of 0.8 mm ID for eluant delivery and another of 0.51 mm ID for buffer delivery providing eluant delivery at a rate of 3.2 ml/min and a 3/1 eluant to buffer ratio. These lines were inserted in the peristaltic pump, as illustrated in FIG. 3, without breaking any connections. Eluant consisting of 1.8M NaCl, 0.2M HCl in sterile pyrogen free water was transferred to the sterile pyrogen free eluant reservoirs in a laminar flow hood. Transfer was accomplished using a sterile transfer set (Burron Medical Inc., Bethlehem, Pa.) and a 35 ml syringe. The solution was filtered through a 0.2 µm sterile pyrogen free filter (Baxa Corporation, Englewood, Colo.). Buffer solution consisting of 1.2M NaOAc was prepared and transferred to its reservoir using identical techniques. These reservoirs were attached to the plumbing set within a laminar flow hood. The generator column was equilibrated prior to loading by pumping 20 ml of eluant continuously through the column. Loading was performed by pumping $^{62}$Zn in 2 ml 2M HCl through the filter with an external peristaltic pump into the load port at a rate of 0.25 ml/min and followed by 3 ml of 2M HCl again at a 0.25 ml/min flow rate. The column was then immediately flushed with 20 ml of eluant using the internal peristaltic pump at a rate of 3.2 ml/min. The generator was then allowed to equilibrate for 30 minutes, and eluted with a volume of 2 ml of eluant.

Generator Performance—Yield, Breakthrough and Isotopic Purity. A total of four large scale generators were produced and thoroughly tested. Two of these (Z1 and Z2) were evaluated in house while the other two (Z3 and Z4) were processed, loaded and shipped overnight to another researcher for evaluation. The two in house units were constructed from targets irradiated to levels of 10 µA-hr and 12.5 µA-hr at 40 MeV while the two shipped units were irradiated at a level of 25 µA-hr at 40 MeV and 33 MeV respectively. The generator yield performance of these units eluted with a volume of 2 ml of eluant (40 second elution time) is determined. Yields consistently range from 90–99% with no indication of fall-off over two days of use.

The level of $^{62}$Cu available at 8:00 am and 5:00 pm of the first day of use for the larger shipped unit was 35 mCi and 18 mCi respectively. These represent clinically useful levels. The $^{62}$Zn breakthrough of the generators proved to be below the measurement limits of HPGe spectroscopy. On two smaller units tested in-house $^{62}$Zn could not be detected on the day after elution by HPGe spectroscopy. This places the level below about $10^{-6}$ mCi. Breakthrough measurements were performed on the shipped units utilizing high sensitivity well counting at 511 keV. All of these measurements were below $10^{-5}$% of available $^{62}$Zn on the column. On generator Z4, the largest generator constructed, a 10,000 second HPGe spectrum was obtained on the first elution of this generator at 12.8 hours post EOB. The elution syringe was positioned on the surface of the HPGe detector. No detectable $^{62}$Zn was found to be present. The upper limit decayed to EOB was 0.0003 µCi. This places the breakthrough upper limit at <1.5×$10^{-7}$%. The dominant isotopes present in this spectrum are $^{66}$Ga (9.4 h) and $^{67}$Ga (78 h). A very small but detectable level of $^{119m}$Te (16 h) is also present. These isotopes are likely produced by p,n reactions on Zn and Sb contaminants in the target foil respectively. The levels of these isotopes decay corrected to the following morning (8:00 am) which would have been the beginning of clinical use, were 0.02 µCi, 0.001 µCi and 0.0001 µCi, respectively. These levels are of negligible concern from the point of view of patient dosimetry. However it is clearly important to assess such contaminant isotopes produced in any given source of copper foil material and assure that their presence is below an acceptable level.

The astonishingly low level of $^{62}$Zn breakthrough is of negligible concern since the patient dose produced by it represents a minute fraction of the injected $^{62}$Cu dose.

Chemical purity can also be quickly verified by performing $^{62}$Cu-PTSM synthesis utilizing a low concentration of $H_2$-PTSM. Repeated reliable synthesis of $^{62}$Cu-PTSM with greater than 99% yield was demonstrated at a level of 0.5 µg/ml of ligand. If cold copper levels are present above 0.1 µg/ml the efficiency of this synthesis will be detectably reduced. Such a test can be very quickly applied prior to generator shipment to verify both absence of cold Cu contamination in the eluant and buffer solutions as well as from loaded $^{62}$Zn.

The $^{62}$Zn/$^{62}$Cu generator system was evaluated for the extent of $^{62}$Cu-PTSM synthesis with an amount of $H_2$PTSM of 10 µg which is a level compatible with human injection, and also of 1 µg $H_2$PTSM per injection volume, and synthesis of the $^{62}$Cu in the eluate to $^{62}$Cu-PTSM complex was found to be near 100% within a reaction time ranging from 4.5–37.5 seconds.

It was concluded that reliable, high-efficiency synthesis of 62Cu-PTSM was possible at a level of 1 µg/injection. The automated micro-mixing provided by the combination of buffer and ligand with eluant containing $^{62}$Cu is evidently very rapid and thorough, providing a substantial time and convenience saving compared to techniques in which ligand is added to a large volume $^{62}$Cu sample and vortex mixing is required. The level of 1 µg/injection of $H_2$-PTSM is easily compatible with toxicity issues for human use.

The $^{62}$Zn isotope with which the anion exchange resin is loaded has a half-life of 9.26 hours, so as the generator ages the radioactivity level of the generator declines as the $^{62}$Zn parent decays into the $^{62}$Cu daughter isotope which in turn decays according to its 9.7 minute half-life. At any given moment in the lifetime of the $^{62}$Zn/$^{62}$Cu generator the equilibrium concentration of $^{62}$Cu available in the generator is an amount that provides a radioactivity level from $^{62}$Cu which is equivalent to of the radioactivity level of the $^{62}$Zn, and from about 90 to about 99% of this $^{62}$Cu is available to be eluted from the generator column by an acidic eluant of high chloride concentration, namely one of a pH of from about 1.0 to about 2.0 and a chloride concentration of at least about 1N Cl and 3N Cl⁻, and preferably 2.0N Cl⁻.

The $^{62}$Zn/$^{62}$Cu generator is constructed with a minimum amount of anion exchange resin so that the $^{62}$Cu available for elution from the generator may be eluted therefrom by a minimum volume of the high chloride concentration eluant. Further, this minimizes the time needed to accomplish the elution of the available $^{62}$Cu. Since the clinically useful level of $^{62}$Cu for PET imaging is from about 1 to about 50 mCi per I.V. bolus injection and it is desirable to maintain the injection volume to a quantity equal to the maximum possible intake into the subject, typically less than 30 cc, it is preferred to elute the $^{62}$Cu available from the generator with an amount of eluant solution that provides for an eluate having a radioactivity level of from about 0.3 to about 5.0 mCi/ml. Use of a peristaltic pump, as illustrated in FIG. 3, to pump the solution in the quantities required through the column to elude $^{62}$Cu then modify it into a useful form, preserves the sterile pryogen free nature of the fluids that come to comprise the physiological isotonic solution used for PET imaging.

Once eluted, it is preferred to work the $^{62}$Cu up into the $^{62}$Cu-ligand complex that is needed for PET imaging as rapidly as possible. Hence the $^{62}$Cu eluant is immediately admixed with a buffering solution to adjust and buffer the so-mixed solution to a pH of from about 5.0 to about 7.0. This buffered solution is then immediately combined with a quantity of the water/ethanol-ligand compound solution that provides about 1 to about 5 µg of ligand compound and admixed therewith by flowing through a length of coiled section of the transfer tubing, after which the concentration of this mixture is reduced to a physiologically isotonic level (i.e. about 0.15N) by metering thereinto the requisite amount of sterile water. Compounds that may be used as the ligand for forming the $^{62}$Cu-ligand complex are represented by the following formula:

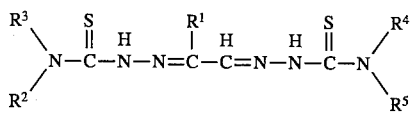

wherein $R^2$, $R^3$, $R^4$ and $R^5$ independently are hydrogen or —CH$_3$ and $R^1$ is a $C_1$-$C_3$ alkyl group. Preferred compounds are those of the formulae:

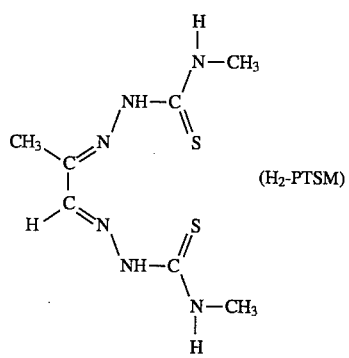

(H$_2$-PTSM)

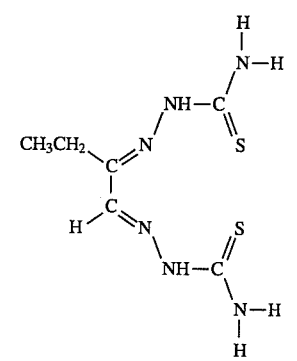

(H$_2$-ETS)

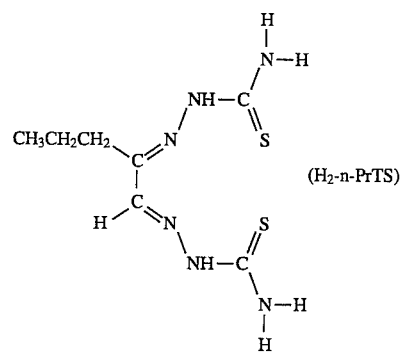

(H$_2$-n-PrTS)

Compounds of this formulation may be prepared by the procedures described in E. K. John et al, *Journal of Medicinal Chemistry*, Vol. 33, No. 6, pp. 1764–1770 (1990). For use in preparing the $^{62}$Cu-ligand complex, the ligand compound is prepared as a water/ethanol (5 to 50% solution in a concentration of from about 1 to about 5 µg ligand compound per milliliter of water/ethanol, and as needed a quantity of the ligand compound water/ethanol solution is metered into admixture with the buffered $^{62}$Cu eluant to provide from about 0.5 to about 5.0 µg of the ligand compound, and preferably no greater than about 1.5 µg of ligand compound.

The solutions employed to elute $^{62}$Cu and synthesize it into a $^{62}$Cu-ligand complex may differ from those as described above. That use as eluant may derive its chloride content solely from the HCl needed for the requisite acidity, though this is less preferred since a greater quantity of buffering solution would then be required to buffer the eluate to the desired pH range of 5.0–7.0. The buffering compound of the buffering solution can be other than sodium acetate, namely it could be sodium citrate, or a sodium citrate-sodium hydroxide mixture. However, sodium acetate is the preferred buffering compound. In all cases the solutions employed should be sterile pyrogen free solutions.

Although the invention has been described with reference to its preferred embodiments those of skill in the art may from this description appreciate changes that may be made which do not depart from the scope and spirit of the invention as described above or claimed hereafter.

What is claimed is:

1. A method for preparing a radiopharmaceutical in a form suitable for intravenous bolus injection, comprising:

eluting $^{62}$Cu from a column of anion exchange resin loaded with $^{62}$Zn in an amount to provide a radioactivity level of from about 0.1 to about 1000 mCi of $^{62}$Zn by forcing an eluant having a pH of less than 2.0 and a chloride ion content of from about 0.5 to about 4.0M over said anion exchange resin to provide an eluate having a radioactivity of from about 1 to about 1000 mCi;

buffering said eluate to a pH value of from about 5.0 to about 7.0 by addition of sodium acetate to provide a buffered eluate having a radioactivity of from about 1 to about 1000 mCi;

mixing the buffered eluate with a ligand solution comprising as a ligand a compound of the formula:

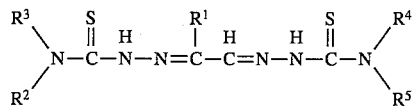

wherein $R^1$ is a lower alkyl radical and $R^2$, $R^3$, $R^4$ and $R^5$ are each independently a hydrogen or a lower alkyl radical and as a solvent water containing from about 5 to about 50 volume % ethanol, said ligand being present in said solvent in a concentration of from about 0.1 to about 10.0 μg/ml, and the ligand solution being present in an amount to provide from about 0.1 to about 10 μg of ligand compound; and adding water to the buffered eluate-ligand solution mixture in an amount sufficient to produce a physiologically isotonic solution acceptable for intravenous injection.

2. The method of claim 1 wherein the ligand compound is pyruvaldehyde bis($N^4$-methylthiosemicarbazone).

3. The method of claim 2, wherein the ligand solution is present in an amount to provide about 1.5 μg or less of ligand compound.

4. The method of claim 3, wherein the physiologically isotonic solution acceptable for intravenous injection has a radioactivity of about 1 to about 50 mCi.

5. The method of claim 4, wherein the physiologically isotonic solution has a volume of 30 cc or less.

6. The method of claim 1, wherein the $^{62}$Zn amount is about 500 mCi or less.

7. The method of claim 1, wherein the physiological isotonic solution is a sterile pyrogen free solution.

8. The method of claim 1, wherein said eluant, said buffering solution, said ligand solution and water are flowed into admixture with each other by action of a peristaltic pump.

* * * * *